(12) United States Patent
Paul et al.

(10) Patent No.: US 6,277,257 B1
(45) Date of Patent: *Aug. 21, 2001

(54) ELECTROKINETIC HIGH PRESSURE HYDRAULIC SYSTEM

(75) Inventors: Phillip H. Paul, Livermore; David J. Rakestraw, Fremont; Don W. Arnold, Livermore; Kenneth R. Hencken, Pleasanton; Joseph S. Schoeniger, Oakland; David W. Neyer, Castro Valley, all of CA (US)

(73) Assignee: Sandia Corporation, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/271,687

(22) Filed: Mar. 18, 1999

Related U.S. Application Data (63) Continuation-in-part of application No. 08/882,725, filed on Jun. 25, 1997, now Pat. No. 6,013,164.

(51) Int. Cl.[7] ..................................................... B01D 61/44
(52) U.S. Cl. .......................... 204/450; 204/600; 204/647; 204/648
(58) Field of Search ................................... 204/450, 600, 204/647, 648

(56) References Cited

U.S. PATENT DOCUMENTS 6,013,164 * 1/2000 Paul et al. ............................ 204/450

FOREIGN PATENT DOCUMENTS

WO99/16162   4/1999 (WO).

* cited by examiner

Primary Examiner—Arun S. Phasge
(74) Attorney, Agent, or Firm—Donald A. Nissen (57) ABSTRACT

An electrokinetic high pressure hydraulic pump for manipulating fluids in capillary-based systems. The pump uses electro-osmotic flow to provide a high pressure hydraulic system, having no moving mechanical parts, for pumping and/or compressing fluids, for providing valve means and means for opening and closing valves, for controlling fluid flow rate, and manipulating fluid flow generally and in capillary-based systems (Microsystems), in particular. The compact nature of the inventive high pressure hydraulic pump provides the ability to construct a micro-scale or capillary-based HPLC system that fulfills the desire for small sample quantity, low solvent consumption, improved efficiency, the ability to run samples in parallel, and field portability. Control of pressure and solvent flow rate is achieved by controlling the voltage applied to an electrokinetic pump.

28 Claims, 4 Drawing Sheets

ELECTROKINETIC HIGH PRESSURE HYDRAULIC SYSTEM

CROSS-REFERENCE TO RELATED APPLICATIONS

This application is a Continuation-in-Part of prior U.S. patent application Ser. No. 08/882,725 filed on Jun. 25, 1997 now U.S. Pat. No. 6,013,160 and entitled ELECTROKINETIC HIGH PRESSURE HYDRAULIC SYSTEM from which priority is claimed.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

BACKGROUND OF THE INVENTION

This invention pertains generally to a method for producing high pressures, by converting electric potential to hydrodynamic force, that requires no moving mechanical parts and particularly to the use of electro-osmotic flow to produce a high pressure system for compressing and manipulating fluids, in general, and in packed microchannels and capillaries, in particular.

The phenomenon of electro-osmosis, in which the application of an electric potential to an electrolyte in contact with a dielectric surface produces a net force on a fluid and thus a net flow of fluid, has been known since Reuss in 1809. The physics and mathematics defining it and its associated phenomenon streaming potential, both part of a larger class of electrochemical phenomena, namely electrokinetic effects, have been extensively explored, *Introduction to Electrochemistry*, S. Glasstone, 1942, pp. 521–529 and R. P. Rastogi, "Irreversible Thermodynamics of Electro-osmotic Flow", *J. Sci. and Industrial Res.*, 28, 284, 1969. In like manner, electrophoresis, the movement of charged particles through a stationary medium under the influence of an electric field, has been extensively studied and employed in the separation and purification arts.

The use of electro-osmotic flow has been wide spread and has found wide ranging applications in chemical analysis. The use of electro-osmostic flow for fluid transport in packed bed capillary chromatography was first documented by Pretorius, et. al., "Electro-osmosis—A New Concept for High-Speed Liquid Chromatography", *J. Chromatography*, 99, 23–30, 1974. Although the possibility of using this phenomenon was recognized two decades ago, the effective use of this method to perform chemical analysis has only recently been demonstrated and has just begun to provide commercial utility.

Except for very general references to the fact that pressures generated by electro-osmotic flow were linearly proportional to the applied voltage (cf. Dasgupta and Liu, *Analytical Chemistry*, 1194, 66, 1793 and Theeuwes U.S. Pat. No. 3,923,426 at col. 1 line 23) there appeared to be no recognition in the prior art that electro-osmosis could be used to generate high pressure. Experimental studies that did explore the relationship between electroosmosis and pressure, generally studies of streaming potential, were limited to pressures below 1 psi (Rastogi, ibid. and Cooke, *J. Chem. Phys.*, 1995, 23, 2302). Moreover, Rastogi, ibid., 291, has shown that the then recognized linear dependence of electro-osmotic pressure and applied electric potential begins to fail at voltages of about 300 to 400 Volts and pressures above about 0.2 to 0.3 psi and, in fact, pressure begins to approach an asymptote of between 0.3 to 0.4 psi at an applied electric potential on the order of 600 Volts. Thus, prior art did not recognize and, in fact, taught away from being able to achieve pressures above about 1 psi by means of electro-osmosis. It is believed that the cause of the non-equilibrium pressure/applied electric potential effects observed in earlier work may be the result of using capillaries having too large a diameter and/or solutions having too high a conductivity which can cause undesirable heating of the electrolyte to the point where boiling and bubble formation can take place.

High-performance liquid chromatography (HPLC) is an established analytical technique that relies on high-pressure mechanical pumps (generally a gear- or cam-driven pump capable of generating pressures in excess of 5,000 psi) to drive a fluid sample through a specially prepared column. The HPLC separation medium or stationary phase is typically a thick bed packed with fine particles. Fused silica beads are often used as an HPLC column packing material. However, fused silica alone is not in general a good separation medium. Usually, a special coating is applied to the particles or the particles themselves are porous. HPLC columns can also be packed with special polymers or resins. Regardless of the column packing used, the HPLC column presents a very large resistance to flow, hence the need for high pressures to drive the sample being analyzed through the system. In HPLC the high pressure pump itself can not only comprise a substantial component of the system but also, because of the need to fill the pump as well as attendant reservoirs and plumbing, can require the use of relatively large samples. However, this proves to be particularly cumbersome in those instances where it is desired to run a second sample or samples in parallel in columns having different stationary phases because of the requirement for separate pumps for each column. Finally, there is a desire to have field-portable instruments which has been frustrated by the size, bulk, and power consumption of conventional HPLC pumps as well as the large amounts of sample required.

Conventional HPLC systems typically employ separation columns of about 3–5 mm in diameter and flow rates ≈3–5 mL/min. However, miniaturization of the separation column (microbore columns) offers several advantages, including improved efficiency, mass detection sensitivity, low solvent consumption, small sample quantity, and easier coupling to detector such as mass spectrometers and flame-based detectors and several analytical methods using miniaturized or capillary columns have been developed for micro-HPLC and capillary electrochromatography (CEC). These columns generally have inside diameters of 1 mm or less.

Commercially available HPLC systems typically employ piston or cam-driven pumps to pressurize the column. However, it is difficult to adapt these pumps to provide the low flow rates under high pressure required for microbore HPLC systems. As a practical matter, cam-driven pumps with the desired stroke ratios cannot be designed for flow rates lower than about 50 $\mu$l/min. A further disadvantage of cam-driven pumps is that a single pump can only provide a limited range of flow rates. This is because different flow rate ranges require cams of substantially different size and the position of the cam relative to the motor and piston is determined by the cam dimensions. Changing the positions of the motor and piston to accommodate a cam of different size is impractical because of the sensitive alignment required in piston pumps.

A alternate approach for pumping in microbore HPLC systems is the syringe-type piston pump. While this type of pump is capable of delivering solvent at a few μl/min flow rate it is difficult to maintain a constant flowrate due to the continuously changing flow resistance.

What is required is a system that will provide pressure driven flows at constant and controllable flow rates, wherein the flow rate can be in the range of mL/min to μl/min. Further, the system must be compatible with microbore columns and the desire for small sample quantity, low solvent consumption, improved efficiency, the ability to run samples in parallel, and field portability.

SUMMARY OF THE INVENTION

The present novel invention uses electro-osmotic flow to provide a high pressure hydraulic system, having no moving mechanical parts, for pumping and/or compressing fluids, for providing valve means and means for opening and closing valves, for controlling fluid flow rate, and manipulating fluid flow generally and in capillary-based systems (Microsystems), in particular. Moreover, because of the compact nature of the inventive high pressure hydraulic pump it is now possible to construct a conventional or capillary-based HPLC system that fulfills the desire for small sample quantity, low solvent consumption, improved efficiency, the ability to run samples in parallel, and field portability. Control of pressure and solvent flow rate is achieved by controlling the voltage applied to an electrokinetic pump.

Figure 1:
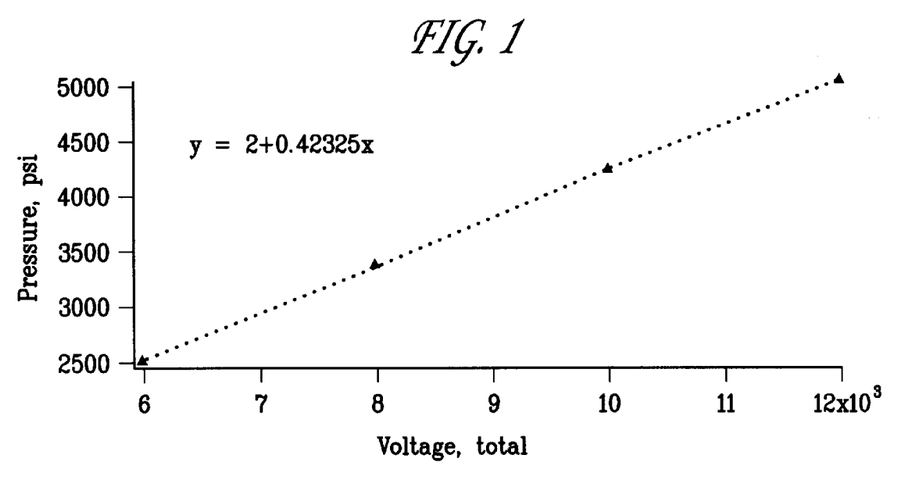
FIG. 1 illustrates the relationship between applied electric potential and pressure generated by the present invention.

Contrary to prior art teachings, the inventors have discovered by both theoretical prediction and experimental studies that in a capillary-based system electro-osmotic flow can generate pressures as high as 5,000 psi and that the relationship between electro-osmotic pressure and applied electric potential is linear up to and including pressures as high as 5,000 psi (FIG. 1).

The ability to pressurize a fluid by means of an electric potential provides a means for imparting net power to the fluid and by this means to transmit and use this net power to perform work (apply force) on some system. It will be appreciated that the ability to convert the hydraulic action produced by the system disclosed herein to mechanical action and work can encompass exerting hydraulic pressure on a diaphragm or hydraulic drive of a positive displacement fluid motor, or hydraulic flexure of a fluid-filled member, or expansion or contraction of a fluid-filled bellows, or extension or retraction of a fluid-filled piston, or any other means known in the art of converting hydraulic action, power and work to mechanical action, power and work.

The inventive high pressure hydraulic pump, hereinafter known as an electrokinetic pump or EKP, comprises at least one tube or channel, that can be a capillary channel or microchannel, forming a fluid passageway containing an electrolyte and having a porous dielectric medium disposed therein between one or more spaced electrodes. The porous dielectric medium can include small particles, high surface area structures fabricated within the microchannel, or microporous materials. An electric potential is applied between the electrodes that are in contact with the electrolyte, that can be aqueous or an organic liquid or mixtures thereof, to cause the electrolyte to move in the microchannel by electro-osmotic flow. The electric field applied across the EKP by the electrodes will cause the electrolyte contained in the porous dielectric medium to flow and presented with an external flow resistance will create a pressure at the down stream end of the EKP. The flowrate of the electrolyte is proportional to the magnitude of the applied electric field (V/m applied across the EKP) and the pressure generated is proportional to the voltage across the device. The direction of flow of the electrolyte is determined by both the nature of the electrochemical interaction between the porous dielectric medium and the electrolyte and the polarity of the applied electric potential. In contrast to prior art hydraulic pumps, and HPLC pumps in particular, the present invention can be realized by integrating part or all of the described components on a chip or micro-scale device, i.e., a device wherein the components have dimensions less than about 0.1 mm. Thus, the EKP is a compact and efficient device which converts electric power to hydraulic power in the working fluid and has been shown to be capable of generating hydraulic pressures greater than 5000 psi. The EKP has been fully described in prior co-pending U.S. patent application Ser. No. 08/882,725 entitled "Electrokinetic High Pressure Hydraulic System" filed Jun. 25, 1997, incorporated herein in its entirety.

The above-described electrokinetic high pressure hydraulic system has several advantageous features. There are no moving mechanical parts and all liquid seals, thus the system is not subject to frictional wear. Since the system is driven electrically and has no moving mechanical parts it can be rapidly turned on and off. By applying periodic electrical potentials, whose periods can be various functions of time, to a plurality of spaced electrodes different timing arrangements such as might be useful for varying compression and valving cycles can be effected. Because a porous dielectric medium with a pore size of between about 2–200 nm presents a very high resistance to pressure driven flow, the high pressure hydraulic system disclosed here acts as a form of check valve when, having achieved a high pressure, the electric potential is switched off. Moreover, the system is capable of remote operation.

In one aspect, the invention is configured such that an electrolyte contained in a porous dielectric medium disposed within a capillary or microchannel can act as a valve; the electrolyte being selectively moveable between a first position opening communication between a fluid inlet and an outlet and a second position closing communication between the fluid inlet and outlet. Opening and closing the valve is provided by applying an electric potential between the spaced electrodes sufficient to cause the electrolyte to move from the first position to the second. The process can be reversed simply by reversing the polarity of the electric potential. By providing an actuator at the fluid outlet it is possible to transfer the hydraulic force generated by the invention into rotary or rectilinear motion. Furthermore, it is contemplated that the hydraulic force developed at an actuator can be transferred to more than one hydraulic line.

In a second aspect, the invention is configured to compress a fluid, which can be either a liquid or a gas. Here a fluid outlet can be either completely sealed or constricted such that when an electric potential is applied between spaced electrodes, movement of the electrolyte causes the fluid which resides between the electrolyte and the sealed or constricted outlet to be compressed.

In a third aspect of the present invention, the EKP and an HPLC column are connected such that the pressure developed by the EKP is applied to the inlet of an HPLC column. The HPLC can be connected directly to the EKP or connection can be made indirectly such that the force developed by the EKP is applied to the HPLC column through a secondary means, such as a positive displacement pump that can be a bellows, diaphragm or piston pump.

It will be appreciated by those skilled in the art that it is desirable to eliminate the generation of any gases that could arise as a consequence of electrolysis of the EKP electrolyte. This can be accomplished by several means known to the art. By way of example, a section of ultra micro-porous material, such as the porous glass sold under the trademark VYCOR, having nominally 4 nm pores, or a membrane such as that sold under the trademark NAFION saturated with electrolyte can be interposed between the electrode providing connection to the high pressure fluid junction and the junction itself. The ultra micro-porous material carries the current but the pores are sufficiently fine that pressure-driven or electro-osmotic flow is negligible.

BRIEF DESCRIPTION OF THE DRAWINGS

The accompanying drawings, which are incorporated in and form part of the specification, illustrate the present invention and, together with the description, explain the invention. In the drawings like elements are referred to by like numbers.

DETAILED DESCRIPTION OF THE INVENTION

The present invention discloses a novel compact high pressure hydraulic pump having no moving mechanical parts that employs electro-osmotic flow to generate high pressure for pumping and/or compressing liquids or gases, for providing valve means, and manipulating fluid flow generally.

For the purpose of describing the invention disclosed herein the term microchannel, as used hereinafter, will refer to a flow channel whose internal dimensions can be on the order of tens to hundreds of microns. Generally, these microchannels are referred to as capillaries, however, the flow channels contemplated by this invention can have an arbitrary cross-sectional geometry, in addition to the circular cross-section conventionally associated with capillaries, and can be fabricated from any material providing that the material is not an electrical conductor.

It is contemplated that the present invention can be advantageously used in microsystems (i.e., systems having dimensions on the order of tens to hundreds of microns) for fluid manipulation generally and, in particular, for compression/expansion of gases and high pressure injection of fluids. The present invention can also find advantageous use as a miniature vacuum pump or a miniature hydraulic pump and particularly for HPLC. Moreover, because the present system exhibits only a very small dead volume it can be used for precise handling of gases.

In order for the electro-osmotic forces useful for this invention to be generated it is necessary that a porous dielectric medium be present in at least one of the microchannels. It is known in the art that an electric double layer is formed at the interface between a solid and a liquid containing ions. As a consequence of the formation of the electric double layer, an electrically charged diffuse layer is formed extending from the solid-liquid interface into the bulk of the liquid. While a double layer can be formed anytime a liquid containing ionic species comes into contact with a solid surface, its physical manifestation is most easily observed in capillary systems. Under the influence of a tangential electric field the diffuse layer is caused to move and will flow at a constant rate depending upon the equilibrium established between frictional forces developed between the moving liquid and the wall of the capillary and the electro-osmotic force generated due to the electric forces acting on the excess ionic charge in the diffuse layer. If the liquid, under the influence of electro-osmotic forces, is allowed to accumulate at the outlet end of the capillary an excess hydrostatic pressure can be developed which can eventually counterbalance the electro-osmotic forces. The inventors have shown, contrary to prior art teachings, that in a capillary-based system electro-osmotic flow can generate pressures at least as high as 5,000 psi and that the relationship between the pressure generated by electro-osmotic flow and applied electric potential is linear up to and including pressures as high as 5,000 psi (FIG. 1).

In addition to solutions containing ions, it is known that pure organic liquids can also form double layers and, thus can be employed to generate electro-osmotic forces. The term "pure" organic liquid refers to organic liquids having a conductivity less than about $10^{-8}$ (ohm-cm)$^{-1}$ and which do not decompose in the presence of the dielectric materials used to construct the EKP or in the presence of a high electric field. It has been discovered by the inventors that, in general, the class of non-aqueous fluids that: 1) are chemically stable; 2) form double layers in contact with solid dielectric materials such as silica, titania, alumina, and organic polymeric materials, either solid or porous, can be used as electrolytes in the EKP application. Organic liquids such as acetonitrile, methanol, ethanol and toluene have been found to be particularly useful as electrolytes for EKP applications as have mixtures of organic liquids and aqueous electrolyte solutions.

By using pure organic liquids as the electrolyte in conjunction with conventional dielectric materials, such as microporous silica beads or microporous methacrylate-based polymer beads to construct an EKP it has been found that the result is a substantial increase in the effective zeta potential and substantial decrease in ohmic current. This, in turn, leads to a substantial increase in power conversion efficiency. Thus, pure organic electrolyte materials provide several advantages in EKP applications:

1) An increase in both pumping performance and efficiency due to an increase in zeta potential.

2) A reduction in ohmic heating and other parasitic losses due to the substantial decrease in ionic conductivity experienced with pure organic electrolytes.

3) A reduction in gas generation at the electrodes due to the decreased ionic conductivity of the organic electrolyte in comparison with conventional aqueous electrolytes.

4) An increase in fluid flowrate, for a given current, through the EKP due to the substantial decrease in conductivity in the pure organic electrolyte. This phenomenon arises as a consequence of the dependence of flowrate on $1/\sigma$, wherein $\sigma$ is the conductivity of the electrolyte.

Dielectric materials useful for this invention can take a number of forms in addition to the more conventional silica structures such as beads or frits. Such structures can be fabricated, by way of example, by lithographic patterning and etching, direct injection molding, sol-gel processes, and high energy lithography combined with electroforming and molding (LIGA) as well as organic polymeric materials, either solid or porous.

The preferred embodiments of this invention, illustrating all their features, will now be discussed in detail. The embodiments of this invention, shown in the accompanying drawings, depict the novel and nonobvious EKP system that uses electro-osmotic flow to provide a high pressure hydraulic system, having no moving mechanical parts, to generate high pressures and constant and controllable flow rates that are especially useful for HPLC.

Figure 2A:
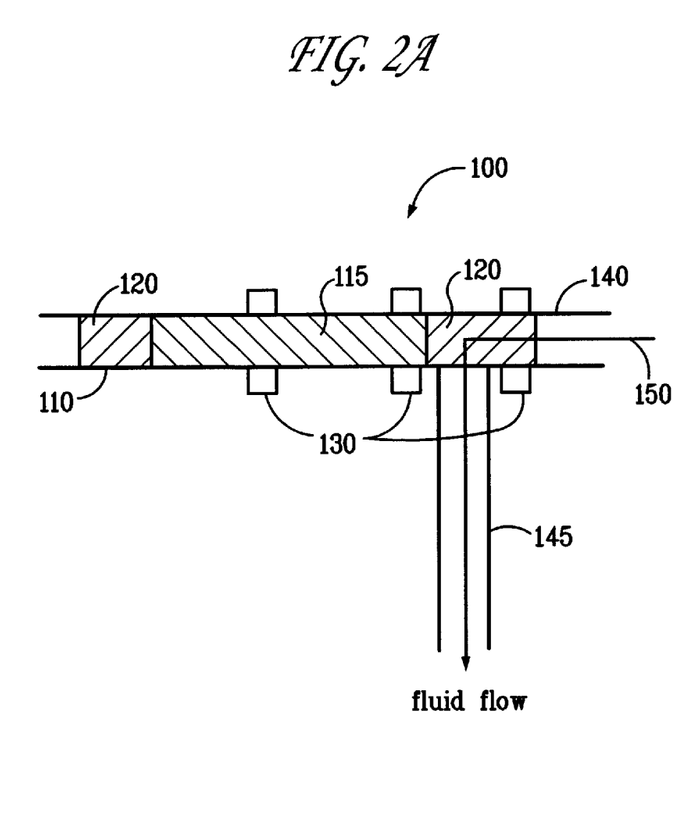
FIG. 2 illustrates a valve embodiment of the present invention.

A valve embodiment of the present invention can be illustrated by reference to FIG. 2(a). Valve 100 comprises a T-shape flow system, wherein microchannel 110 contains a porous dielectric 120, extending past outlet 145 about 1–2 channel diameters, that can include fine particles, preferably silica having a diameter of about 100 nm to 5 $\mu$m, or other high surface area features such as might be produced by microfabrication methods known to those skilled in the art, preferably by lithographic etching, and which present a porous matrix having a high surface area for electrolyte solution 115 to flow through. Fluid inlet 140 and outlet 145 in communication with the outlet of microchannel 110 provide for the flow of a fluid (liquid or gas) 150 therethrough.

Figure 2B:
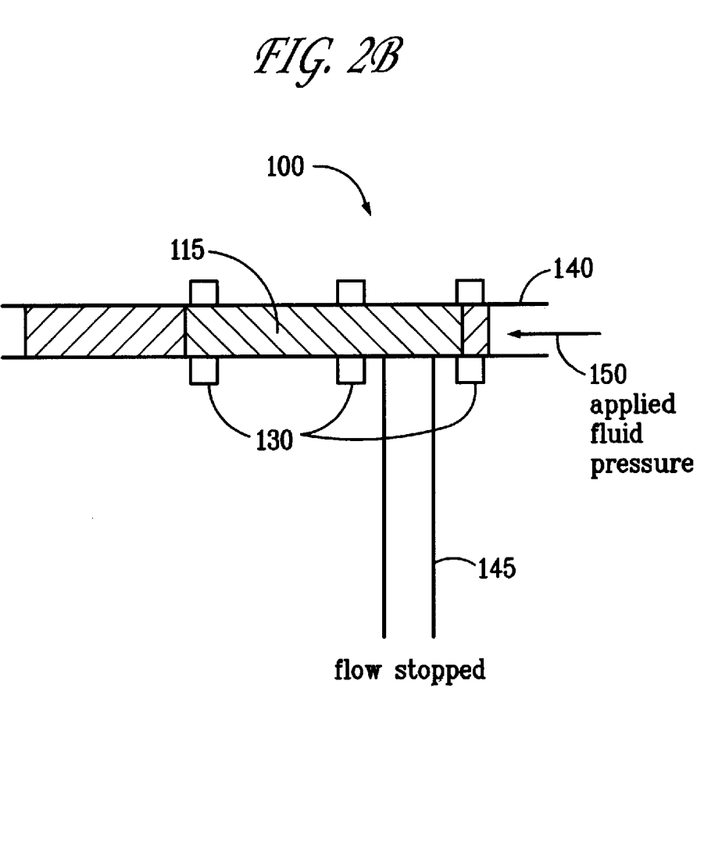

Referring now to FIG. 2(b), in order to close communication between fluid inlet 140 and outlet 145 an electric potential is applied by a power supply (not shown) to spaced electrodes 130 to provide the electro-osmotic force required to move electrolyte 115, to cover and thus close fluid outlet 145, and prevent fluid 150 from flowing through outlet 145. Valve 100 can be opened by simply reversing the sign of the electric potential applied to spaced electrodes 130.

It is contemplated that the electric potential applied between spaced electrodes 130 can, in addition to the step function form described hereinabove, assume various other forms suitable to the operation of the system described herein such as oscillatory having a varying shape and period.

Figure 3:
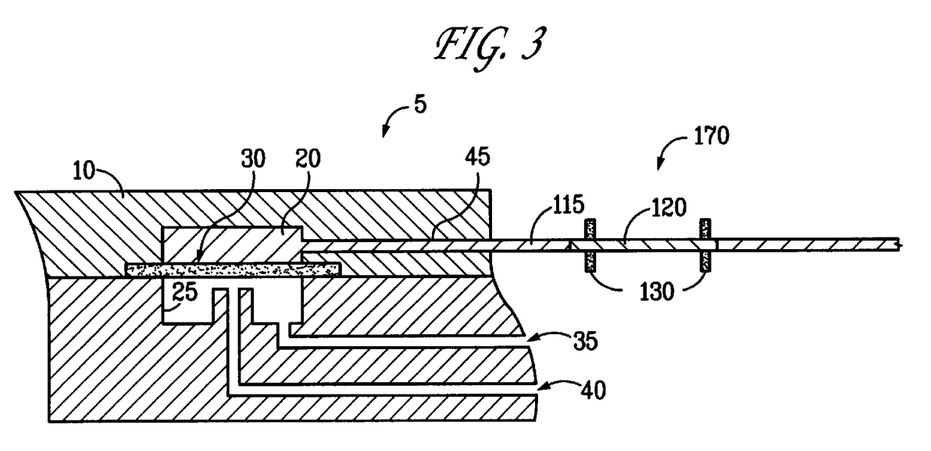
FIG. 3 shows a second valve embodiment.

A second valve embodiment is shown in FIG. 3 that provides for controlling the flow of a fluid that can be either a liquid or a gas. Here, a housing 10 has a cavity formed in its inner surface. The cavity is divided into two chambers 20 and 25 separated by a fluid tight flexible member 30. Flexible member 30 is preferably made from materials that are compatible with fluids that are contained in chambers 20 and 25 and are flexible by virtue of their composition or mechanical design. A fluid stream enters chamber 25 through fluid inlet line 40 and exits through fluid outlet line 35. The flow of the fluid stream is controlled by applying hydraulic pressure generated by electrolyte 115 by the action of electro-osmotic pump 170 through inlet line 45 to the fluid contained in chamber 20 and in turn on flexible member 30 causing it to deform and thereby close off fluid inlet line 40 and stop fluid flow. To open valve 5 the polarity of the electric potential applied to spaced electrodes 130 is reversed. It should be noted that because of the resistance of dielectric medium 120 to pressure driven flow, i.e., a pressure of several thousand psi can be required to force fluid through the dielectric medium, simply shutting the applied electric potential will generally not cause valve 5 to open. Further, because the hydraulic forces generated by the instant invention can be as great as 5000 psi or more this valve is capable of controlling high pressure lines. Moreover, because chamber 20 and inlet line 45 are filled with fluid the addition of only that amount of fluid necessary to cause displacement of flexible member 30 is required and thus, the response time of the valve can be very rapid. The response time of the valve can also be improved by minimizing the dimension between the proximal end of fluid inlet line 40 and flexible member 30.

Figure 4:
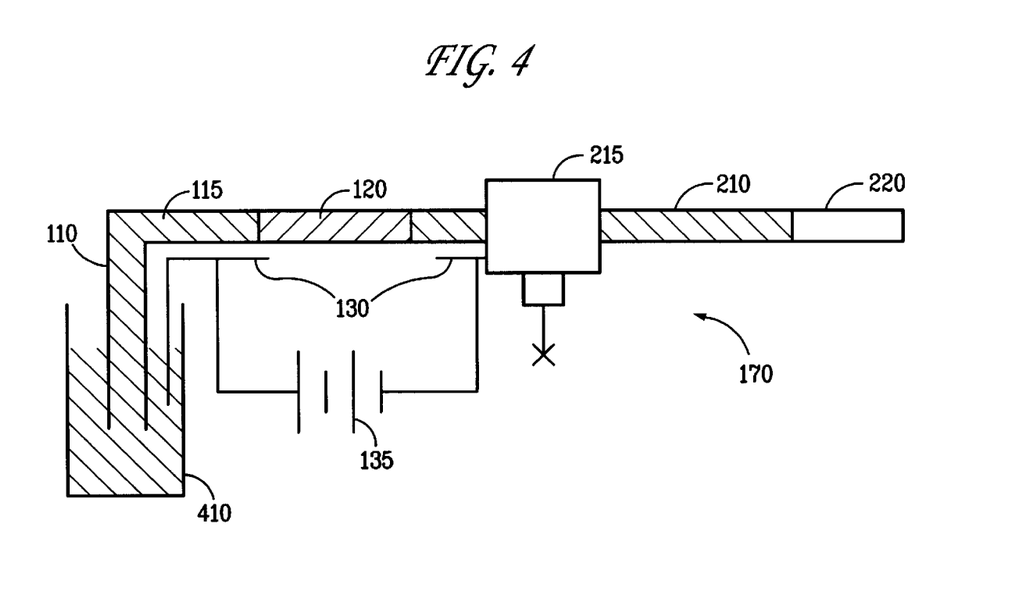
FIG. 4 illustrates a compressor embodiment.

The use of the inventive EKP as a means for compressing a fluid, preferably a gas, within a flow channel can be illustrated by reference to FIG. 4. The inlet end of EKP 170, consisting of microchannel 110, containing porous dielectric material 120, electrolyte 115 and spaced electrodes 130, is submerged in electrolyte 115. The outlet end of EKP 170 is connected one leg of "T" fitting 215. One end of capillary 210 is connected to the opposite leg of fitting 215 and the other end of capillary 210 can be constricted or sealed shut. An electric potential is applied by a power supply 135 connected to spaced electrodes 130 in contact with electrolyte 115. Electro-osmotic forces generated in microchannel 110 cause electrolyte 115 to advance by electro-osmotic pumping into microchannel 110 and further into capillary 210. The further advance of electrolyte 115 is stopped when the pressure of fluid 220, constrained in the sealed end of capillary 210 is high enough to counterbalance the electro-osmotic force produced by the electric potential applied to spaced electrodes 130, i.e., when the pressure of fluid 220 equals the electro-osmotic force generated by the applied electric potential. Shutting off or reducing the applied electric potential can cause electrolyte 115 to retreat until the forces are once again balanced. However, because of the resistance of dielectric medium 120 to pressure driven fluid flow, the pressure at outlet 145 will decrease only very slowly, if at all, under these conditions. Reversing the polarity (sign) of the applied electric potential will provide for more rapid flow reversal.

By way of example, a 15 cm long fused silica capillary 110 having a 75 $\mu$m inside diameter was packed with silica spheres 120 having a diameter of about 3 $\mu$m. The packed column was wetted with electrolyte 115, water buffered with a sodium phosphate buffer to a pH of 8.6. One end of the packed capillary 110 was then submerged into a reservoir 410 that contained electrolyte 115 as well as one of electrode 130. The opposite end of packed capillary 110 was sealed into one leg of HPLC fitting 215 that served as the second electrode 130. One end of an open fused silica capillary 210 was sealed into the remaining leg of HPLC fitting 215. Power was supplied to electrodes 130 causing electrolyte 115 to be electro-osmotically pumped through packed column 110 and into open capillary 210. Having wetted a portion of the open capillary the distal end of open capillary 210 was sealed shut. Power was again supplied to electrodes 130 until sufficient pressure was reached to counterbalance the electro-osmotic pumping force. For an applied field of about 300 V/cm a pressure in excess of 2500 psi was observed in the sealed end of capillary 210.

In addition to using the high pressures generated by the EKP to provide valve means, the EKP provides the ability to generate constant and controllable flow rates and, thus has been shown to be especially useful for HPLC. Since control of pressure and solvent flow rate is achieved by controlling the voltage applied to an electrokinetic pump, by joining together an EKP and an HPLC column in such a fashion that the pressure developed by the EKP can be applied to the inlet of an HPLC column it is now possible to provide a liquid chromatography system that is entirely voltage driven. Thus, it is no longer necessary to use prior art mechanical means for generating the high pressures required for HPLC. The HPLC can be connected directly to the EKP or connection can be made indirectly such that the force developed by the EKP is applied to the HPLC column through a secondary means, such as a positive displacement means that can be a bellows, diaphragm or piston pump. The improvement embodied in this inventive combination now makes it possible to integrate part or all of the described components on a chip or micro-scale device, i.e., a device wherein the components have dimensions less than about 0.1 mm and thus to construct a conventional or capillary-based HPLC system that fulfills the desire for small sample quantity, low solvent consumption, improved efficiency, the ability to run samples in parallel, and field portability.

Figure 5:
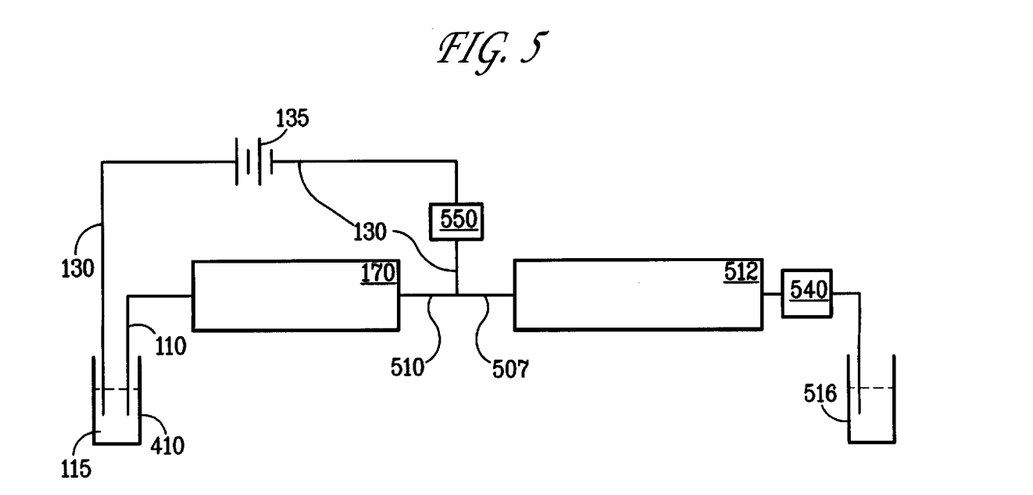
FIG. 5 is an illustration of the invention showing a configuration useful for HPLC.

Referring now to FIG. 5, the inlet end 110 of EKP 170 was placed in a container or reservoir 410 containing a liquid sample or a running buffer 115 and one of spaced electrodes 130. The outlet of the EKP 170 was connected in series with the inlet end 507 of HPLC column 512. The second electrode 130 was connected to the high pressure outlet end 510 of EKP 170. Voltage was applied across EKP 170 from DC power supply 135 which caused buffer fluid 115 from buffer reservoir 410 to flow through the EKP and generated a high pressure at inlet 507 to HPLC column 512. The pressure generated by EKP 170 drove sample 115 through HPLC column 512 to detector 540 located at the outlet end of the HPLC column and into waste reservoir 516. As discussed above, it is preferred to interpose a salt bridge 550 between electrode 130 and the high pressure outlet end of EKP 170. A sample can be introduced into the system by temporarily dipping inlet 110 into a container holding the liquid sample and then returning the EKP inlet to buffer reservoir 410. In the embodiment illustrated in FIG. 5 the sample was introduced into the HPLC system at the inlet of the EKP and, thus the sample introduction means did not have to be high pressure compatible. However, in this embodiment because the sample was directly subject to the electrokinetic effect of EKP 170 this configuration is not suitable for some types of chromatography, such as size exclusion chromatography (SEC).

Figure 6:
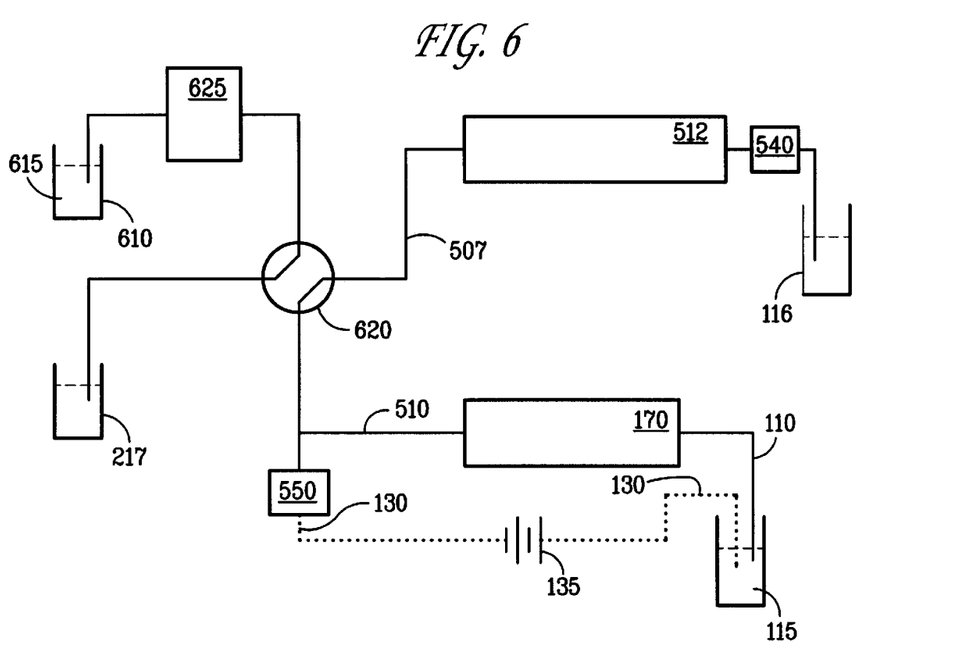
FIG. 6 illustrates a second configuration useful for HPLC.

A configuration such as that illustrated in FIG. 6 is compatible with a chromatographic analysis scheme wherein the sample is not directly subject to electrokinetic effects. Here, sample 615 was introduced into HPLC column 512 by a conventional low pressure pump means 625, such as a syringe, diaphragm, or other type of low pressure pump and a conventional HPLC sample valve 620. After the sample was introduced into the system, valve 620 was rotated to switch the sample to the junction of the high pressure outlet end 510 of EKP 170 and inlet 507 to HPLC column 512. The sample is forced through HPLC column 512 by applying a voltage to EKP 170 as described above.

Figure 7:
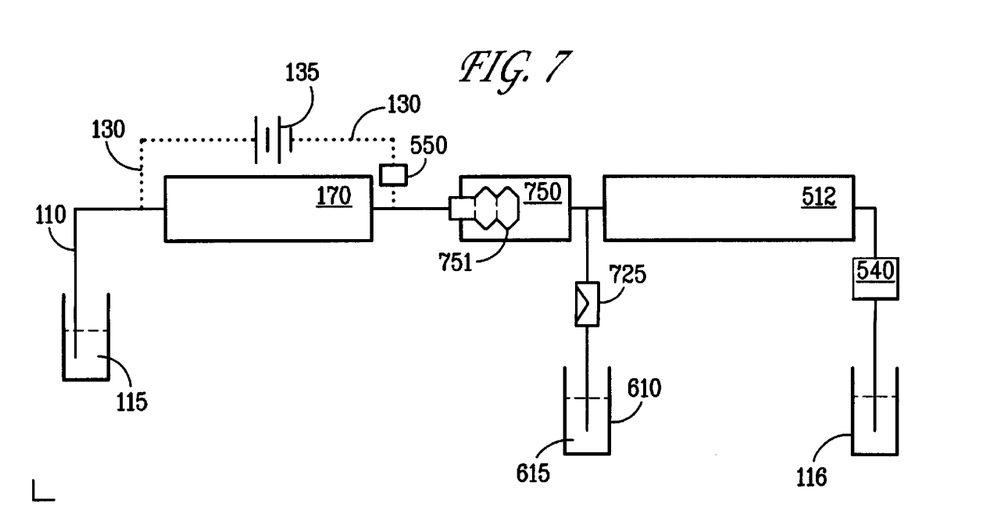
FIG. 7 illustrates third configuration useful for HPLC.

A further embodiment contemplated by the present invention is the use of the EKP to drive a positive displacement pump such as a bellows, diaphragm or moving piston pump. A particular embodiment is illustrated in FIG. 7. Here, EKP 170 can be used to drive a sealed positive displacement pump 750 which, in turn, can be used to draw a portion of sample 615 from reservoir 610 and force it through HPLC column 512. After opening valve 725, bellows 751 is retracted by applying a voltage of the appropriate sign to EKP 170, thereby drawing a portion of sample 615 from reservoir 610. Subsequently, valve 725 is closed and bellows 751 is compressed by reversing the sign of the voltage applied to EKP 170 forcing the sample the sample through HPLC column 512 to detector 540 located at the outlet end of HPLC column 512 and into waste reservoir 116. A second EKP can be used to operate valve 725.

It will be appreciated by those skilled in the art that two electrokinetic pumps can be used in parallel, in a push-pull configuration, to provide the ability to perform a longer separation than can be done using a single stroke of a positive displacement pump. In this configuration one EKP can supply pressure to a corresponding positive displacement element while the other EKP can be operated in reverse to withdraw a displacement element connected thereto thereby filling that element with a fresh charge of fluid. Check valves, or other active valve means known in the art, can be used to switch the outlets of the displacement elements between the source of fluid and the destination, such as a HPLC column. In this configuration the two EKP/displacement element pairs alternate between supplying pressure and refilling, thus allowing a continuous separation to be performed.

Multiple EKPs, operating to drive a separation fluid directly or via a positive displacement element, can be configured in parallel with each pump supplying a different separation fluid to proportioning valves and thence to a mixer. This permits the composition of the separation fluid to be continuously varied as would be required in gradient separation or gradient elution chromatographic methods.

The pressure generated in this system is proportional to the electric potential and scales linearly with the length of the capillary, limited only by power dissipation Or dielectric breakdown, in this context, it should be noted that in the presence of an applied field there will be ohmic heating of the microchannel and its contents and that this ohmic heating will have a substantially radial profile. The combination of a relatively high thermal conductivity aqueous electrolyte and the small physical dimensions involved suggest that there will be only a small radial temperature gradient as a result of this heating. If it is necessary it is straight forward to efficiently remove the heat generated in a microchannel, which can be a fused capillary, using forced air or immersion in a heat transfer liquid.

In summary, the present novel electrokinetic pump is useful generally in any application where manipulation of fluids in microchannels and capillary channels is required, particularly in such applications as remote actuation of valves and other components or where a compressed fluid can be used to drive a fluid charge at high pressure and at a controlled low flow rate.

It will be understood that the above described arrangements of apparatus and the methods pertaining thereto are merely illustrative of applications of the principles of this invention and many other embodiments and modifications can be made by those of skill in the art without departing from the spirit and scope of the invention as defined in the claims.

We claim:

1. A valve for the manipulation of a fluid, comprising:
 a) an electrokinetic pump capable of exerting a hydraulic force greater than 10 psi, consisting of;
   i) a microchannel having a fluid inlet and outlet and a porous dielectric material disposed in said microchannel;
   ii) an electrolyte contained within said microchannel and in communication with the porous dielectric material;
   iii) spaced electrodes in contact with said electrolyte; and
   iv) means for applying an electric potential to said spaced electrodes; and
 b) a housing, including;
   i) a first chamber having at least one fluid inlet and at least one fluid outlet sealingly connected thereto;
   ii) a second chamber containing a fluid and adapted to receive the output from the electro-osmotic pump connected thereto; and iii) a flexible member sealingly separating said first and second chambers and adapted to move in response to the hydraulic force generated by the electro-osmotic pump to close or open the fluid inlet.

2. The valve of claim 1, wherein the electrolyte is a pure organic liquid.

3. The valve of claim 2, wherein the pure organic liquid is selected from the group consisting of acetonitrile, methyl alcohol, ethy 1 alcohol and toluene.

4. The valve of claim 1, wherein the electrolyte is a mixture of an aqueous electrolyte solution and a pure organic liquid.

5. The valve of claim 1, wherein the fluid is a liquid or a gas.

6. The valve of claim 1, wherein the porous dielectric material includes porous dielectric materials fabricated by processes selected from the group consisting of lithographic patterning and etching, direct injection molding, sol-gel processing, electroforming.

7. The valve of claim 1, wherein the porous dielectric material includes organic polymer materials.

8. The valve of claim 1, wherein said means applies an electric potential that varies in time.

9. The valve of claim 1, wherein the direction of the hydraulic force is determined by the polarity of the applied electric potential.

10. An improved high performance liquid chromatography system, the improvement comprising joining at least one apparatus for converting an electric potential to a hydraulic force to a high performance liquid chromatography column to provide an entirely voltage driven liquid chromatography system capable of controlling precisely the composition and delivery of a liquid at low flow rate, wherein the apparatus is capable of exerting a hydraulic force greater than 10 psi and wherein the apparatus consists of:

a) a microchannel having a fluid inlet and outlet and a porous dielectric material disposed in said microchannel;

b) an electrolyte contained within said microchannel and in communication with the porous dielectric material;

c) spaced electrodes in contact with said electrolyte; and d) means for applying an electric potential to said spaced electrodes.

11. The system of claim 10, wherein the porous dielectric material includes silica particles.

12. The system of claim 11, wherein the silica particles have a diameter of between about 100 nm and 5 $\mu$m.

13. The system of claim 10, wherein the porous dielectric material includes porous dielectric materials fabricated by processes selected from the group consisting of lithographic patterning and etching, direct injection molding, sol-gel processing, and electroforming.

14. The system of claim 10, wherein the porous dielectric material includes organic polymer materials.

15. The system of claim 10, wherein the electrolyte is a pure organic liquid.

16. The system of claim 15, wherein the pure organic liquid is selected from the group consisting of acetonitrile, methyl alcohol, ethyl alcohol and toluene.

17. The system of claim 10, wherein the electrolyte is a mixture of an aqueous electrolyte solution and a pure organic liquid.

18. The system of claim 10, wherein the apparatus is joined to the high performance liquid chromatography column by positive displacement means.

19. The system of claim 10, further including means for applying an electric field to the high performance liquid chromatography column.

20. A microfluidic device for high performance liquid chromatography, comprising: a solid substrate fabricated to define a microchannel disposed therein, the microchannel comprising, in combination, an electrokinetic pump joined to a high performance liquid chromatography column, wherein the electrokinetic pump consists of;

a) a porous dielectric material disposed in said microchannel;

b) an electrolyte contained within said microchannel and in communication with said porous dielectric material;

c) spaced electrodes in contact with said electrolyte; and d) means for applying an electric potential to said spaced electrodes.

21. The device of claim 20, wherein the porous dielectric material includes silica particles.

22. The device of claim 21, wherein the silica particles have a diameter of between about 100 nm and 5 $\mu$m.

23. The device of claim 20, wherein the porous dielectric material includes porous dielectric materials fabricated by processes selected from the group consisting of lithographic patterning and etching, direct injection molding, sol-gel processing, and electroforming.

24. The device of claim 20, wherein the porous dielectric material includes organic polymer materials.

25. The device of claim 20, wherein the electrolyte is a pure organic liquid.

26. The device of claim 25, wherein the pure organic liquid is selected from the group consisting of acetonitrile, methyl alcohol, ethyl alcohol and toluene.

27. The device of claim 20, wherein the electrolyte is a mixture of an aqueous electrolyte solution and a pure organic liquid.

28. The device of claim 20, further including means for applying an electric field to the high performance liquid chromatography column.

* * * * *